US00PP10607P

United States Patent [19]

Austin

[11] Patent Number: Plant 10,607

[45] Date of Patent: Sep. 22, 1998

[54] SHRUB ROSE PLANT NAMED 'AUSLED'

[75] Inventor: David Charles Henshaw Austin, Wolverhampton, England

[73] Assignee: David Austin Roses Limited, Albrighton, England

[21] Appl. No.: 788,554

[22] Filed: Jan. 24, 1997

[51] Int. Cl.[6] ..... A01H 5/00

[52] U.S. Cl. ..... Plt./1

[58] Field of Search ..... Plt./1, 22, 26

*Primary Examiner*—Howard J. Locker

*Attorney, Agent, or Firm*—Klarquist Sparkman Campbell Leigh & Whinston, LLP

[57] ABSTRACT

A new and distinct variety of shrub rose plant having a unique combination of full, peachy-pink flowers with rosette formation; disease resistance; attractive shrubby growth; and repeat flowering.

1 Drawing Sheet

The present invention relates to a new and distinct variety of shrub rose plant of the rosa hybrida class which was originated by me by crossing the variety Ausblush (unpatented) with an unnamed seedling.

The primary objective of this breeding was to produce a new shrub rose variety having disease resistance and shrubby growth with very repeat flowering of attractive flowers. The objective was substantially achieved, along with other desirable improvements, as evidenced by the following unique combination of characteristics that are outstanding in the new variety and that distinguish it from its parents, as well as from all other varieties of which I am aware:

1. Attractive, full, peachy-pink flowers with rosette formation;
2. Very disease resistant;
3. Repeat flowers well;
4. Attractive shrubby growth.

Asexual reproduction of this new variety by budding, as performed at Albrighton, Wolverhampton, England shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Ausblush (unpatented).

*Pollen parent.*—Unnamed seedling.

Classification:

*Botanical.*—Rosa hybrida.

*Commercial.*—Shrub.

Flower

Observations made from specimens grown in a garden/greenhouse environment at Albrighton, Wolverhampton, England in July 1996.

Blooming habit: Recurrent.

Bud:

*Size.*—About 20–25 mm long when the petals start to unfurl.

*Form.*—The bud form is medium length, globular with pointed top.

*Color.*—When sepals first divide, bud color is Red Group 48A. When half brown, the upper sides of the petals are Yellow Group 9D; and the lower sides of the petals are Red Group 39D and lightening to Yellow Group 9D.

*Sepals.*—Color: Green Group 141C. Surface texture: Hairy and waxy. There are three lightly appendaged sepals. There are two unappendaged sepals with hairy edges.

*Receptacle.*—Color: Green Group 413C. Shape: Funnel. Size: Medium (about 6 mm—8 mm). Surface: Smooth.

*Peduncle.*—Length: Medium (about 45 mm to 60 mm). Surface: Slightly rough. Color: Greyed-Purple 183B. Strength: Bending.

Bloom:

*Size.*—Large. Average open size is about 76 mm.

*Borne.*—Several together in clusters of irregular shape of up to six blooms.

*Stems.*—Medium, normal. Average length is about 450–550 mm.

*Form.*—When first open: Shallowly cupped. Permanence: Flattens, outer petals curl back.

*Petalage.*—Number of petals under normal conditions: Average 86.

*Color.*—The upper sides of the petals are Yellow-White Group 158C and Red Group 56B toward the edges on some petals. The reverse sides of the petals are Red Group 36D. The base of each petal is Yellow Group 8A. The major colors on the upper sides are Yellow-White Group 158C and Red Group 36B.

*Variegations.*—None.

*Discoloration.*—The general tonality at the end of the first day: No change. At the end of the third day: Red Group 36B pales with age to Red Group 36D.

*Fragrance.*—Strong.

Petals:

*Texture.*—Thin.

*Shape.*—Outer petals round. Inner petals deltoid.

*Form.*—Tips slightly recurved.

*Arrangement.*—Quartered, with no petaloids in the center.

*Persistance.*—Petals drop off cleanly before drying.

*Lastingness.*—On the plant: Long (about 5 days). As a cut flower: Not tested.

Reproductive parts:

*Anthers.*—Size: Small. Quantity: Many. Color: Yellow. Arrangement: Regular round styles.

*Filaments.*—Color: Yellow.

*Pollen.*—Color: Gold yellow.

*Styles.*—Color: Light green.

*Stigmas.*—Color: Yellow.

Form: Shrub.

Growth: Vigorous; branching; mature plant is about 122 cm high and 77 cm wide.

Foliage: Number of leaflets on normal mid-stem leaves: 7.

*Size.*—Medium (about 65 mm long×40–50 mm wide).

*Quantity.*—Normal.

*Color.*—New foliage: Upper surface: Greyed Purple. Group 185A. Lower surface: Greyed-Purple Group 183B. Old foliage: Upper surface: Green Group 139A. Lower surface: Yellow-Green Group 147B.

Leaflets:

*Shape.*—Pointed oval.

*Texture.*—Upper side: Slightly glossy.

*Edge.*—Serrated.

*Serration.*—Single, small.

*Petiole rachis.*—Color: Reddish.

*Petiole underside.*—There are three to five small prickles (Greyed-Red Group 182A) between which are many minute protruberances which give the petiole a rough feel.

*Stipules.*—Medium, glandular, hairy and serrated (about 25 mm long from tip to where it joins stem).

*Disease resistance.*—Resistant to mildew and black-spot under normal growing conditions at Albrighton, Wolverhampton, England.

Wood:

*New wood.*—Color: Reddish. Bark: Smooth.

*Old wood.*—Color: Green. Bark: Smooth.

Prickles:

*Quantity.*—On main canes from base: Ordinary (mainly toward the base of the stem). On laterals from main canes: Ordinary.

*Form.*—Medium, straight.

*Color when Young.*—Greyed-Purple Group 183A.

Small Prickles:

*Quantity.*—On main stalks: Very few. On laterals: Many.

*Color.*—Greyed-Orange Group 174B.

I claim:

1. A new and distinct variety of shrub rose plant of the rosa hybrida class, substantially as herein shown and described, characterized particularly as to novelty by the unique combination of its full, peachy-pink flowers with rosette formation; disease resistance; attractive shrubby growth; and repeat flowering.

* * * * *

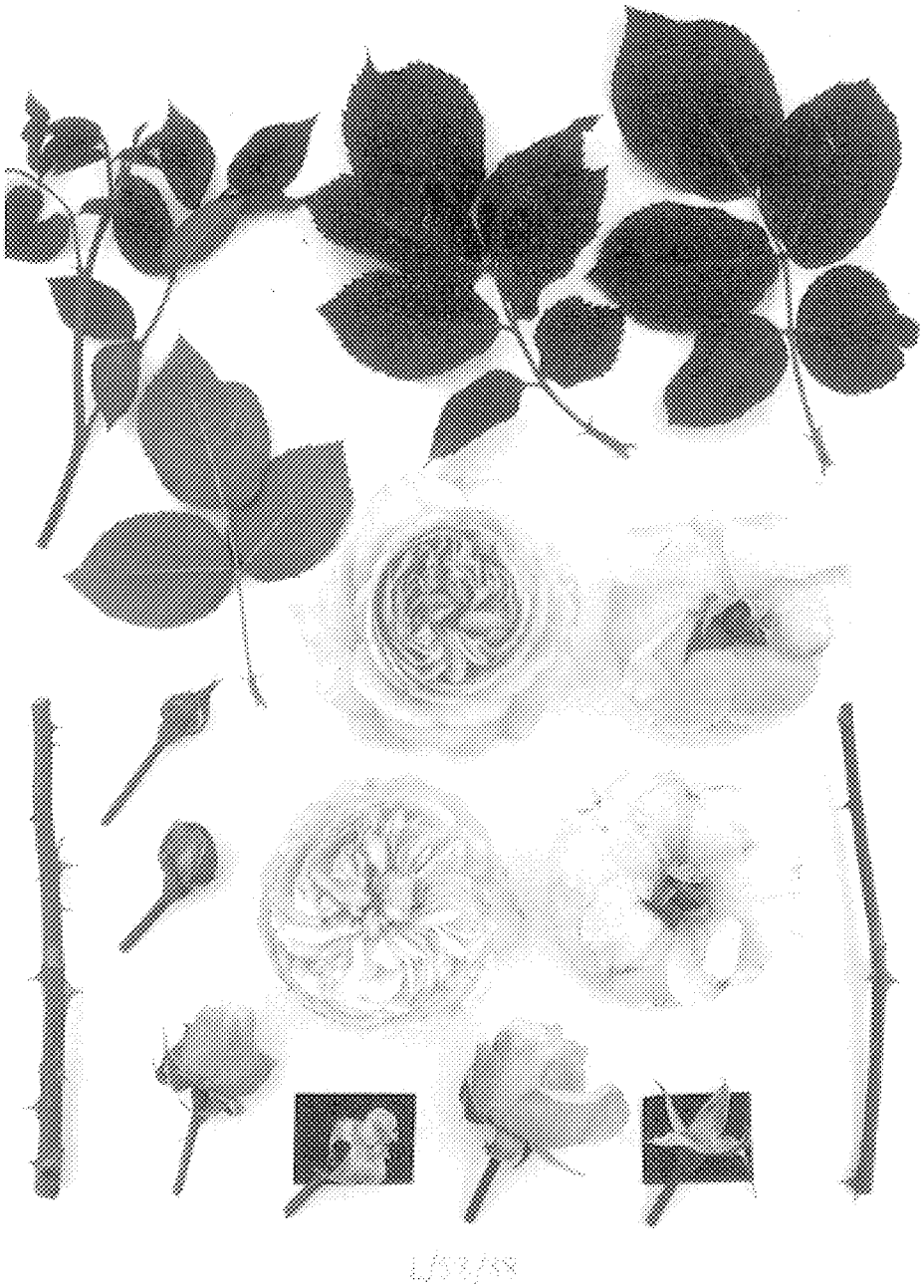

UNITED STATES PATENT AND TRADEMARK OFFICE

CERTIFICATE OF CORRECTION

PATENT NO. : PP 10,607

DATED : September 22, 1988

INVENTOR(S) : D.C.H. Austin

It is certified that error appears in the above-identified patent and that said Letters Patent is hereby corrected as shown below:

In column 2, line 7, change "brown" to --blown--.
In column 2, line 14, change "413C" to --143C--.
In column 2, line 15, change "6mm - 8mm" to --6mm x 8mm--.

In column 4, line 7, after "Reddish." add --Greyed-Purple Group 183A.--
In column 4, line 8, after "Green." add --Yellow-Green Group 146B.--

Signed and Sealed this

Thirtieth Day of November, 1999

*Attest:*

*Attesting Officer*

Q. TODD DICKINSON

*Acting Commissioner of Patents and Trademarks*